United States Patent [19]

Hanaoka et al.

[11] 4,447,559

[45] May 8, 1984

[54] MULTI-LAYER ION EXCHANGER FOR USE IN ION-EXCHANGE CHROMATOGRAPHY AND METHOD OF PRODUCING THE SAME

[75] Inventors: Yuzuru Hanaoka; Takeshi Murayama; Setsuo Muramoto, all of Musashino, Japan

[73] Assignee: Yokogawa Hokushin Electric Corporation, Tokyo, Japan

[21] Appl. No.: 397,060

[22] Filed: Jul. 12, 1982

Related U.S. Application Data

[63] Continuation-in-part of Ser. No. 390,208, Jun. 21, 1982, abandoned.

[30] Foreign Application Priority Data

Jul. 30, 1981 [JP] Japan ................................ 56-119689

[51] Int. Cl.³ ............................................. C08D 5/20
[52] U.S. Cl. ...................................................... 521/28
[58] Field of Search .......................................... 521/28

[56] References Cited

U.S. PATENT DOCUMENTS

| | | | |
|---|---|---|---|
| 3,485,658 | 12/1969 | Jles ......................................... | 521/28 |
| 3,957,698 | 5/1976 | Hutch ..................................... | 521/28 |
| 4,101,460 | 7/1978 | Small et al. ............................ | 521/28 |

Primary Examiner—Joseph L. Schofer
Assistant Examiner—Peter F. Kulkosky
Attorney, Agent, or Firm—Moonray Kojima

[57] ABSTRACT

An ion exchanger comprising a carrier comprising a synthetic resin having no ion exchange group and having one or more particles of a predetermined size, and a plurality of ion exchange particles disposed on the surface of the carrier and bonded thereto by a binder, wherein the plurality of ion exchange particles are of sizes smaller than the sizes of the carrier particles, and wherein the binder is of a synthetic resin having the same or similar composition as that of the carrier. The ion exchanger is useable in ion chromatography systems.

3 Claims, 3 Drawing Figures

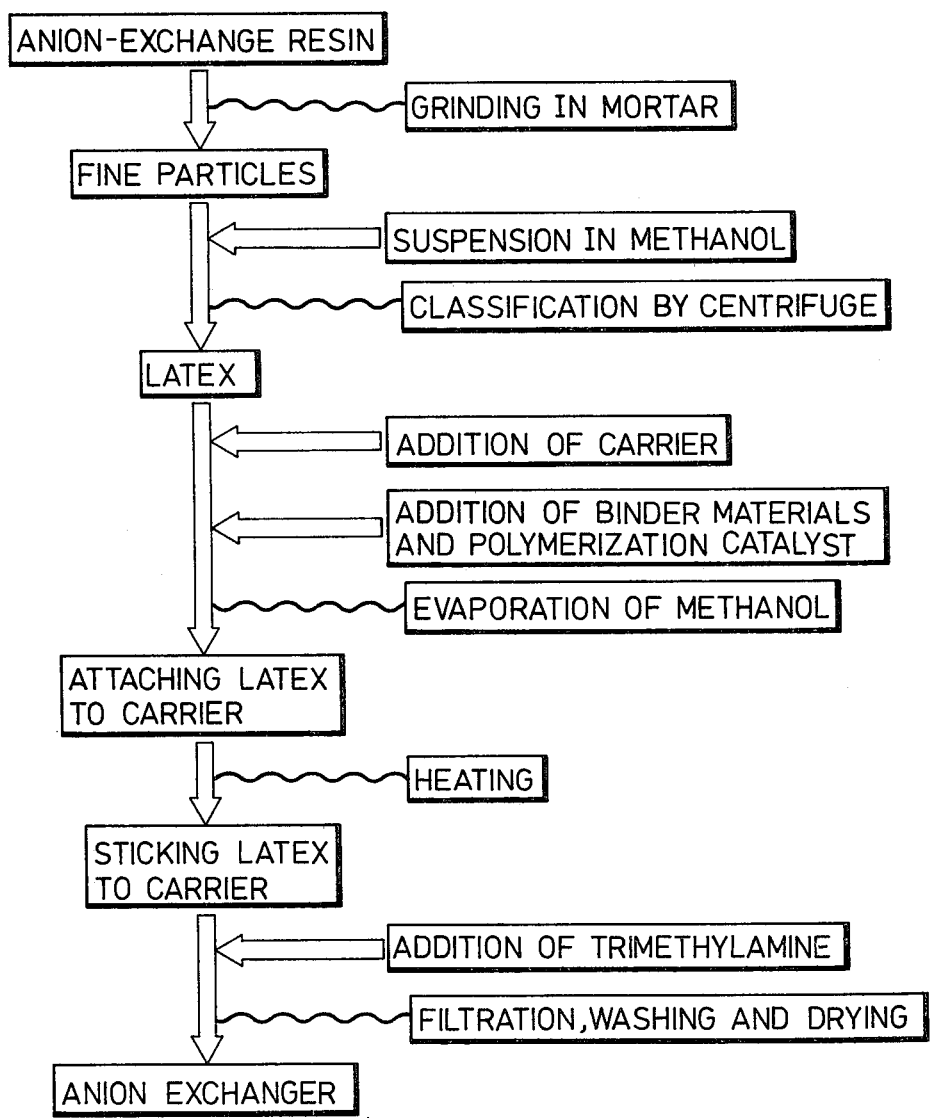

MULTI-LAYER ION EXCHANGER FOR USE IN ION-EXCHANGE CHROMATOGRAPHY AND METHOD OF PRODUCING THE SAME

This is a continuation-in-part of Ser. No. 390,208, filed June 21, 1982, now abandoned.

BACKGROUND OF THE INVENTION

1. Field of the Invention.

This invention relates to an ion exchanger which may be employed in ion chromatography systems for analysis of anions in a sample solution using ion-exchange chromatograph, and to a method of producing the same.

2. Description of the Prior Art.

In ion chromatography systems for analysis of anions in sample solutions using ion exchange chromatographs, there have usually been employed ion exchangers consisting of ion exchange resins as a stationary phase. When an eluent (or mobile phase) is flowing through the ion exchanger, the ion-exchanger resin of a stationary phase exists in a state coupled with opposite ions existing in the eluent. If a sample solution is injected into the ion-exchange chromatograph in such a state, each ion contained in the sample solution undergoes, upon the passing through the ion exchanger, an ion-exchange reaction with the opposite ion coupled with the ion-exchange resin. As a result, each ion is distributed between the eluent (or mobile phase) and the ion exchanger (or stationary phase). Differences in moving rates of ions could develope because the distribution varies with the kind of ions, that is, the affinity for an ion exchanger differs depending on the kinds of ions. Accordingly, ions could be separated in a column packed with an ion exchanger.

It is therefore, no exaggeration to say that an ion exchanger, which has the above described function, determines the capabilities of an ion-exchange chromatography system. A good deal of labor and time have been spent on the study and development of ion exchangers which would optimize efficiency and capacity.

One particular ion exchanger has been disclosed in a published Japanese Patent Application No. 50-77290 dated June 24, 1975, and called "Ion-Exchange Composition".

FIG. 1 herein is a cross sectional view depicting a prior art ion exchanger, such as described in the above Japanese Patent Application. Turning to FIG. 1, a carrier 1 consisting of a styrene-divinylbenzene copolymer, has an outer stratum 2 formed by a technique known as sulphonation. A plurality of fine sized particles 3, made for example by pulverizing an anion-exchange resin are disposed over the carrier 1. Each fine particle 3 has anion-exchange groups, and is electrostatically attached and layered onto outer stratum 2, as depicted.

FIG. 2 is an explanatory diagram showing a method of producing a prior art ion exchanger, such as described in the above Japanese Patent Application. Referring to FIG. 2, the surface of carrier 1 comprised, for example of a styrene-divinylbenzene copolymer is sulphonated by use of a sulfuric acid, and by heating. Next, the surface-sulphonated carrier is packed into a column made of a stainless steel tube.

Concurrently, anion-exchange resin is ground in a mortar, in order to produce fine sized particles thereof. These fine sized particles are suspended in some distilled water, to produce a latex (or suspension). After standing for about one hour, the latex is skimmed. Some skimmed latex is refined by means of a centrifugal separator, and then, a refined latex is injected into the column packed with the carrier. The fine sized particles contained in the latex, are successively attached to the carrier. From the latex detected by analyzing the effluent from the column by use of a spectrophotometer, it is then judged that no more particles can be attached to the carrier. Thus, the ion exchanger illustrated in FIG. 1, for example, is completed as packed in a column.

The above mentioned prior art ion exchanger, has a number of deficiencies, such as that the fine sized anion-exchange particles are liable to become detached from the carrier when it is washed by a concentrated alkaline solution flowing through the column holding the ion exchanger. Also, the separation properties of the fine sized anion-exchange particles are liable to deteriorate when coming into contact with the organic components of sample solutions. Moreover, the method of producing such ion exchangers, such as discussed with reference to the flow diagram of FIG. 2, does not permit ready and easy adjustment of capacity of ion exchange. Thus, the column packed with such prior art ion exchangers, is generally inferior in capability for separating ions.

SUMMARY OF THE INVENTION

This invention aims to overcome the above and other deficiencies and disadvantages of the prior art.

An object of this invention is to provide an ion exchanger which is employed in ion-exchange chromatographs and which exhibits stable and large capacity for separating ions, and a method of producing such ion exchangers.

According to the invention, an ion exchanger is so constructed that fine sized synthetic resin particles having anion-exchange groups, are intimately attached to the surface of a carrier comprised of a synthetic resin particle having no ion-exchange group, using a binder comprised of a resin having the same or similar composition as that of the carrier.

BRIEF DESCRIPTION OF DRAWING

FIG. 3 is a cross sectional view depicting an illustrative embodiment of the invention.

FIG. 4 is an explanatory flow diagram depicting a method of producing the embodiment shown in FIG. 3.

DETAILED DESCRIPTION OF PREFERRED EMBODIMENTS

Figure 1:
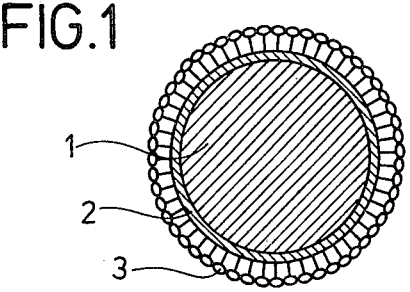
FIG. 1 is a cross sectional view depicting a prior art ion exchanger.
Figure 2:
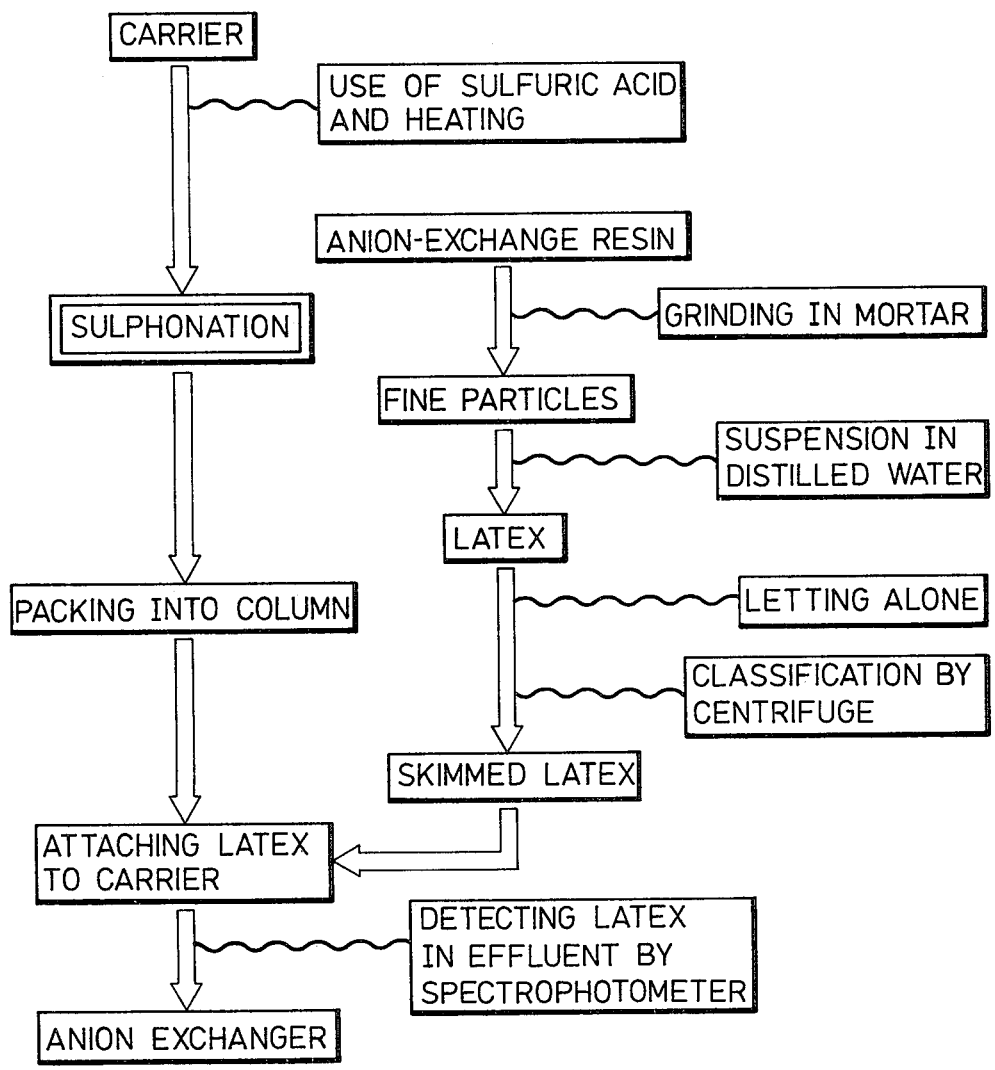
FIG. 2 is an explanatory flow diagram depicting a method of producing the ion exchanger depicted in FIG. 1.

Turning now to FIG. 3, the illustrative ion exchanger comprises a synthetic resin particle 4 having no ion-exchange groups and preferably being of a diameter within the range of from 10 to 20 $\mu$m. The particle 4 acts as a carrier for the fine sized particles 6 having anion-exchange groups, as will be discussed in further detail hereinbelow. The particle 4 may comprise, for example, a styrene-divinylbenzene copolymer or the like. Coated on the carrier 4 with binder 5 are a plurality of fine sized particles 6, which perform the ion exchange function. The binder 5 comprises a resin having the same or similar composition as that of carrier 4, such as, for example, a styrene-divinylbenzene copolymer. The fine sized particles 6 may comprise a synthetic resin having anion-exchange groups and have a diameter preferably within the range of from 0.1 to 0.5 $\mu$m. For example, the fine sized particles, (which for convenience of designation, may be referred to as "separator particles" as distinguished from the particles 4 which for convenience of designation, may be referred to as "carrier particles.") may comprise a styrene-divinylbenzene copolymer or the like. The fine sized particles 6 may be disposed on the carrier particle 4 in a plurality of layers, as depicted, for example, in FIG. 3. The separator particles 6 are intimately attached, bonded or grafted, onto carrier particle 4 by use of binder 5. Although only one carrier particle 4 is depicted, a plurality of such particles 4 can be used as the carrier. A plurality of the ion exchangers shown in FIG. 3, may be packed into, for example, a stainless steel tube or the like, and function as, for example, separation columns as used in ion exchange chromatography systems.

All the components of the ion exchanger shown in FIG. 3 may be comprised of the same synthetic resin, such as styrene-divinylbenzene, or of different synthetic resins. The binder 5 preferably has the same or similar composition as the composition of the carrier 4. The separator particles 6 preferably are fine sized, such as between 0.1 to 0.5 $\mu$m, and are of a composition wherein anion-exchange groups are contained, so that ion-exchange function may be performed thereby. Advantageously, styrene-divinylbenzene copolymer has highly stable mechanical and chemical properties, and is thus, preferable for use in the different components, such as carrier particle, separator particles, and binder.

The ion exchanger, when comprised of synthetic resin having highly stable mechanical and chemical properties, will have the same advantageous properties as the components. Also, the fine sized particles 6 are more firmly and intimately attached or bonded or grafted onto the carrier 4. In contrast, the prior art ion exchangers have separator particles electrostatically attached to an outer stratum of a carrier. Thus, the fine sized particles of this invention are not limited by the deficiencies of the prior art, that is, contrary to the prior art, the fine sized separator particles of the invention are not detected from the carrier when, for example, concentrated sulfuric acid or the like is passed through the ion exchanger.

The inventors have discovered that using a binder having the same or similar composition as the carrier to which a plurality of fine sized particles are intimately attached by the binder, ion exchanging function is readily and efficiently performed and the life time of the ion exchanger is substantially lengthed, in addition to the other advantageous effects which are discussed elsewhere herein.

Referring now to FIG. 4, a method of producing an ion exchanger, such as shown in FIG. 3, will be discussed. Into a mortar or the like, is ground 5g of a strongly basic anion-exchange resin, such as, a styrene-divinylbenzene copolymer or the like, of 200 to 400 mesh, for 12 hours, to produce fine sized particles, for example, of the styrene-divinylbenzene copolymer. 0.4 g of the fine sized particles are then suspended in 200 ml of alcohol, e.g. methanol, in a container, and classified for one hour in a centrifugal separator at about 4,000 r.p.m. Then, the liquid phase (emulsion) is taken out from the suspension into another container. This liquid phase is called "latex".

Concurrently, there is prepared 5 g of a carrier, comprised of styrene-divinylbenzene copolymer particles, having particle sizes within the range of from 10 to 20 $\mu$m, which are then added into the latex.

The latex is heated to about 50° C., in order to evaporate the alcohol component. Before evaporation is completed, a mixture of chloromethylstyrene and divinylbenzene, in the weight ratio of 95:5, and additionally incorporated with 1% of alpha, alpha-azobisisobutyronitrile, is added to the latex. The mixture of chloromethylstyrene and divinylbenzene acts as the binder, and the alpha, alpha-azobisisobutyronitrile acts as a polymerization catalyst.

While the alcohol content is being evaporated, the latex is attached to the carrier particles. Next, the latex is heated to about 80° C. and maintained at the same temperature for about 2 hours, in order to effect polymerization reaction between chloromethylstyrene and divinylbenzene. While the chloromethylstyrene and divinylbenzene copolymer is being produced, the latex is intimately attached to the carrier.

Finally, by adding trimethylamine, chloromethyl groups in the chloromethylstyrene-divinylbenzene copolymer are aminated in order that the hydrophobic characteristic of said copolymer is converted to the hydrophilic one. By this amination, chlorine (—Cl) of the chloromethyl group is substituted with quaternary ammonium (—$N^+(CH_3)_3$) and anion exchange groups are introduced into the surface and outer layer of said copolymer. The ion exchanger as shown in FIG. 3, can be produced by the above mentioned procedure.

Additional steps of washing with 1N hydrogen chloride and water, and followed by drying, are usually conducted as finishing steps, in order to remove contaminants which may be attached to the ion exchanger. The thus produced ion exchanger is packed into columns made for example of stainless steel, such as by a known slurry packing method. The columns thus filled can be used, for example, as separation columns, for incorporation into a ion chromatography system.

As has been described, the ion exchanger according to the invention, can be produced by going through such processes as the adding of carriers, binder material and polymerization catalyst to a latex, and evaporating completely the alcohol component of the latex. The ion exchange capacity of the ion exchanger can be varied as needed. The fine sized particles having any desired ion exchange groups, are intimately attached or bonded or grafted, in any desired amount, onto the surface of the carrier, by suitable selection of amounts and components.

Figure 5:
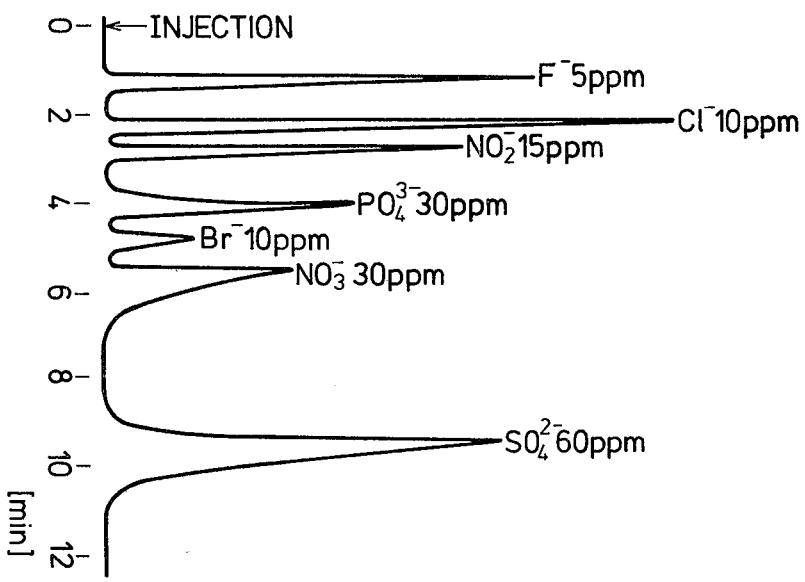
FIG. 5 is a chromatogram obtained using the embodiment of FIG. 3.

FIG. 5 is a chromatogram obtained by using a column packed with the ion exchanger of FIG. 3, with an eluent flowing therethrough at a flow rate of 2 ml/min. and charged with 100 $\mu$l of a standard sample solution containing ion species of 5 ppm of $F^-$, 10 ppm of $Cl^-$, 15 ppm of $NO_2^-$, 30 ppm of $PO_4^{3-}$, 10 ppm of $Br^-$, 30 ppm of $NO_3^-$, and 60 ppm of $SO_4^{2-}$. (This solution is hereinafter referred to as a "standard sample".).

Figure 6:
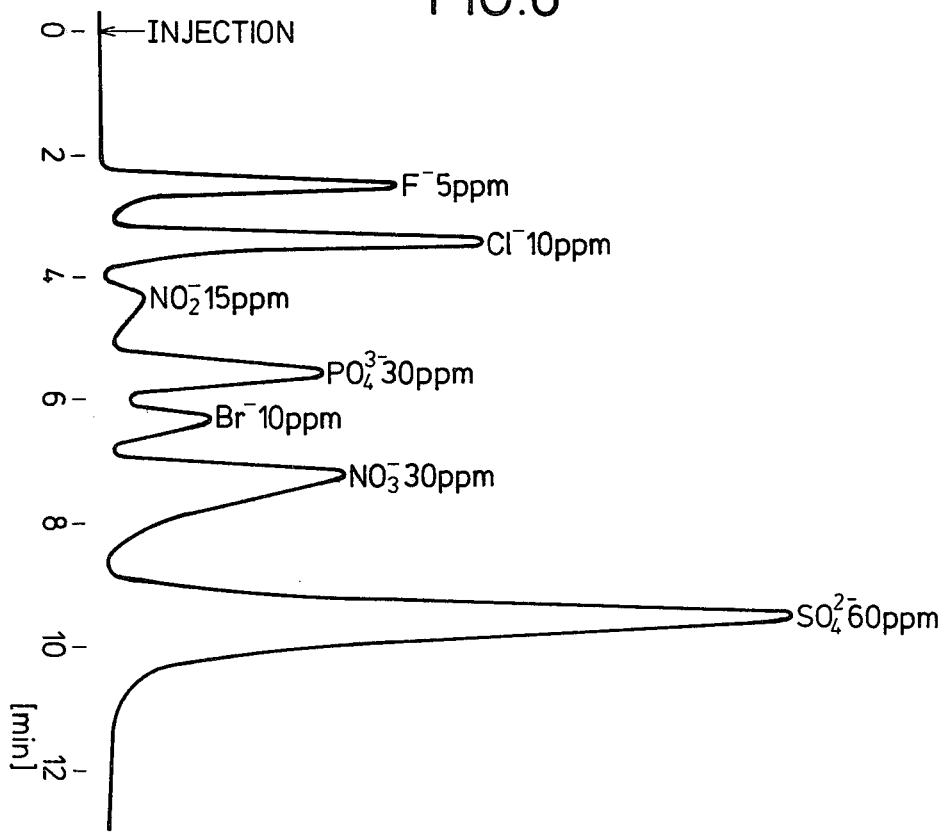
FIG. 6 is a chromatogram obtained using the ion exchanger shown in FIG. 1.

FIG. 6 is a chromatogram obtained by using a column packed with a prior art ion exchanger, such as shown in FIG. 1, with an eluent flowing therethrough at a flow rate of 3.5 ml/min. and charged with 100 $\mu$l of the aboved discussed standard sample.

From a comparison of FIGS. 5 and 6, it can be seen that the ion exchanger of the invention has a greater ion-exchanger reaction rate and a shorter separation time than the one packed with the prior art ion exchanger. In addition, the chromatogram of FIG. 5 has theoretical plate numbers of about 1400 with respect to $SO_4^{--}$ component and about 1700 with respect to $Cl^-$ component, and has narrowed peak widths. Accordingly, increased rates and improved separations can be more readily achieved by the inventive ion exchanger. It is believed that the reason why the ion exchanger of the invention offers the above advantage is that ion exchanger groups exist only within very limited depths from the surface of the carrier.

The colums packed with the inventive ion exchangers show no fluctuations in their choratograms even after being washed for one hour with 1N NaOH, methanol or acetone at a flow rate of 2 ml/min, and had stable elution times as well. This is probably because detachment of the fine sized particles did not take place during the washing since the fine sized particles having ion exchange groups, were firmly attached both mechanically and chemically, to the carrier. Moreover, the carrier particles, the separator particles and binder, were of the same composition.

As has been discussed, the inventive ion exchangers have improved properties because the fine size particles having the anion exchange groups, are intimately attached to limited depths of the surface of the carrier particle, and the same or similar composition is used for the binder and carrier.

The foregoing description is illustrative of the principles of the invention. Numerous modifications and extensions thereof would be apparent to the worker skilled in the art. All such modifications and extensions are to be considered to be within the spirit and scope of the invention.

What is claimed is:

1. A method of producing an ion exchanger for use in ion exchange chromatography, comprising the steps of
    suspending fine sized particles of a styrene-divinylbenzene copolymer into alcohol;
    classifying the resulting suspension using a centrifugal separator;
    taking a classified liquid phase out of said supsension, adding coarse sized styrene-divinylbenzene copolymer particles into said liquid phase, and then evaporating alcohol component by heating said liquid phase at a temperature of about 50° C.;
    adding a mixture of chloromethylstyrene and divinylbenzene having additionally incorporated therein alpha, alpha-azobisisobutyronitrile to said liquid phase, just before completion of said evaporation, and then heating said liquid phase at a temperature of about 80° C., in order to effect polymerization reaction between said chloromethylstyrene and said divinylbenzene; and
    aminating chloromethyl groups in said chloromethylstyrene-divinylbenzene copolymer, by means of trimethylamine treatment, whereby said copolymers are made hydrophilic, and to thereby introduce anion exchange groups into said fine sized particles, wherein said fine sized particles have sizes ranging from 0.1 to 0.5 μm; and wherein said coarse sized styrene-divinylbenzene copolymer particles added to said liquid phase has sizes ranging from 10 to 20 μm; and wherein said polymerization reaction between said chloromethylstyrene and said divinylbenzene produces said chloromethylstyrene-divinylbenzene copolymer which acts as a binder; and wherein said binder is positioned between each of said fine and coarse particles and is grafted onto each particle thereby to form intimate attachment of a plurality of fine particles to each other through mutual attachment to said binder, and to form intimate attachment of a plurality of said fine particles to each coarse particle through mutual attachment to said binder.

2. An ion exchanger for use in ion exchange chromatography systems, consisting essentially of
    a carrier comprising one or more particles of a styrene-divinylbenzene copolymer having no ion exchange group and having a diameter of 10 to 20 microns;
    a binder comprising a styrene-divinylbenzene copolymer resin; and
    a plurality of fine sized particles of a styrene-divinylbenzene copolymer having a diameter of 0.1 to 0.5 micron, and having anion exchange groups,
    wherein said binder is positioned between each of said fine sized particles and said carrier particles and is grafted onto each particle by in situ polymerization onto each particle, thereby to form intimate attachment of a plurality of said fine sized particles to each other through mutual attachment to said binder, and to form intimate attachment of a plurality of said fine sized particles to each carrier through mutual attachment to said binder.

3. The ion exchanger of claim 2, wherein said fine sized particles are attached in a plurality of layers to said surface of said one or more carrier particles.

* * * * *